United States Patent [19]

Ono et al.

[11] Patent Number: 4,784,144
[45] Date of Patent: Nov. 15, 1988

[54] OPTICAL FIBER IMAGE SENSOR

[75] Inventors: Kimizo Ono; Koichi Tsuno; Mitsuru Nishikawa, all of Osaka, Japan

[73] Assignee: Sumitomo Electric Industries, Ltd., Osaka, Japan

[21] Appl. No.: 115,644

[22] Filed: Oct. 26, 1987

Related U.S. Application Data

[63] Continuation of Ser. No. 836,217, Feb. 28, 1986, abandoned, which is a continuation of Ser. No. 519,333, Aug. 1, 1983, abandoned.

[30] Foreign Application Priority Data

| Jul. 31, 1982 | [JP] | Japan | 57-134055 |
| Feb. 23, 1983 | [JP] | Japan | 58-29963 |
| Feb. 24, 1983 | [JP] | Japan | 58-30579 |
| Mar. 9, 1983 | [JP] | Japan | 58-39683 |
| Mar. 18, 1983 | [JP] | Japan | 58-40540[U] |
| Apr. 1, 1983 | [JP] | Japan | 58-58423 |
| Apr. 19, 1983 | [JP] | Japan | 58-68860 |

[51] Int. Cl.⁴ .............................................. A61B 1/06
[52] U.S. Cl. ........................................ 128/634; 128/6; 350/96.26; 350/96.33
[58] Field of Search ............... 128/634, 6, 7, 664–667; 350/96.26, 96.33

[56] References Cited

U.S. PATENT DOCUMENTS

| 3,413,067 | 11/1968 | Froio | 128/6 |
| 3,950,073 | 4/1976 | Horiguchi et al. | 350/96.33 |
| 4,000,416 | 12/1976 | Goell | 250/199 |
| 4,053,756 | 10/1977 | Takahasni | 128/6 |
| 4,086,919 | 5/1978 | Bullard | 128/6 |
| 4,210,029 | 7/1980 | Porter | 128/634 |
| 4,215,678 | 8/1980 | Heing et al. | 128/6 |
| 4,270,840 | 6/1981 | Uchida et al. | 350/96.33 |
| 4,361,139 | 11/1982 | Takagi | 128/6 |
| 4,384,775 | 5/1983 | Hosada | 128/6 |
| 4,390,012 | 6/1983 | Mizumoto | 350/96.26 |
| 4,465,334 | 8/1984 | Sik et al. | 350/96.33 |

Primary Examiner—Edward M. Coven
Attorney, Agent, or Firm—Sughrue, Mion, Zinn, Macpeak, and Seas

[57] ABSTRACT

An optical fiber sensor is composed of an outer portion generally in the form of a tube which constitutes an illumination light transmission path. Inside the tube is formed or inserted an image path for directing image light back to an observation point. A longitudinal hole may be formed beside or surrounding the image path for conducting a fluid to the observed location. The sensor is especially suitable for medical image catheter or endoscopic usage.

37 Claims, 11 Drawing Sheets

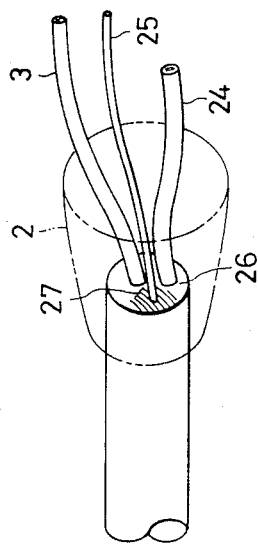
FIG. 9
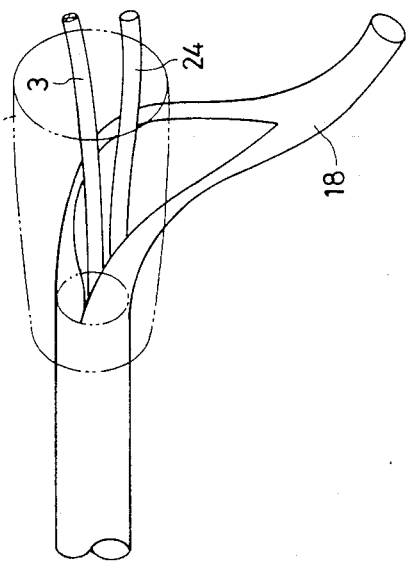
FIG. 10
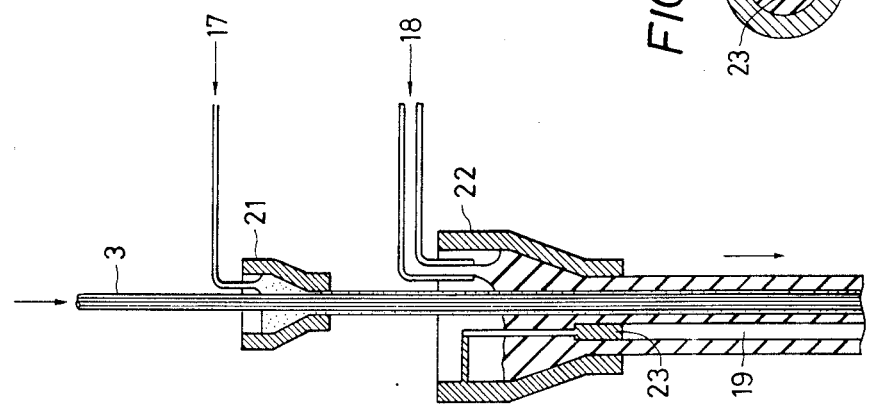
FIG. 7
FIG. 8

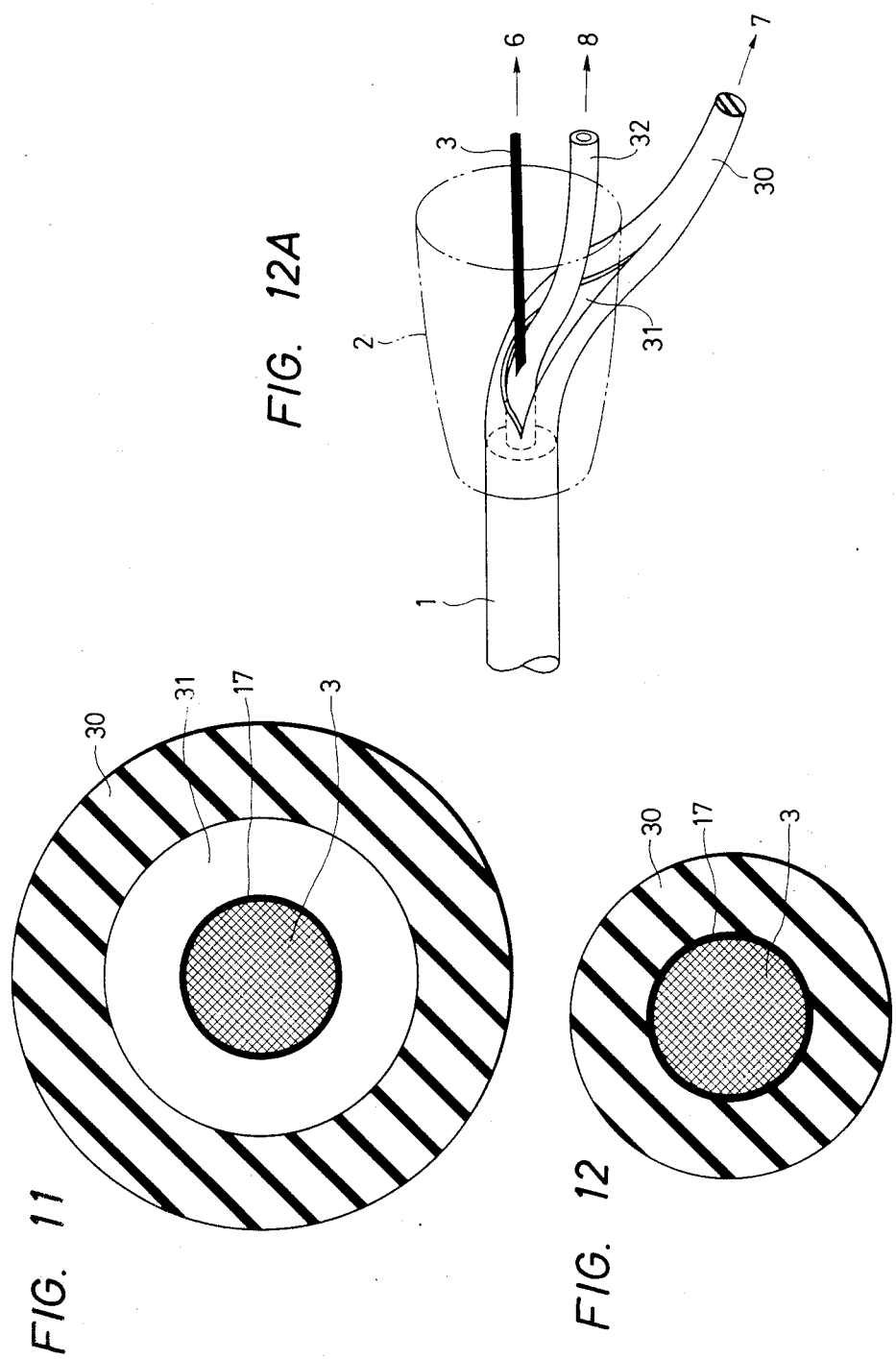

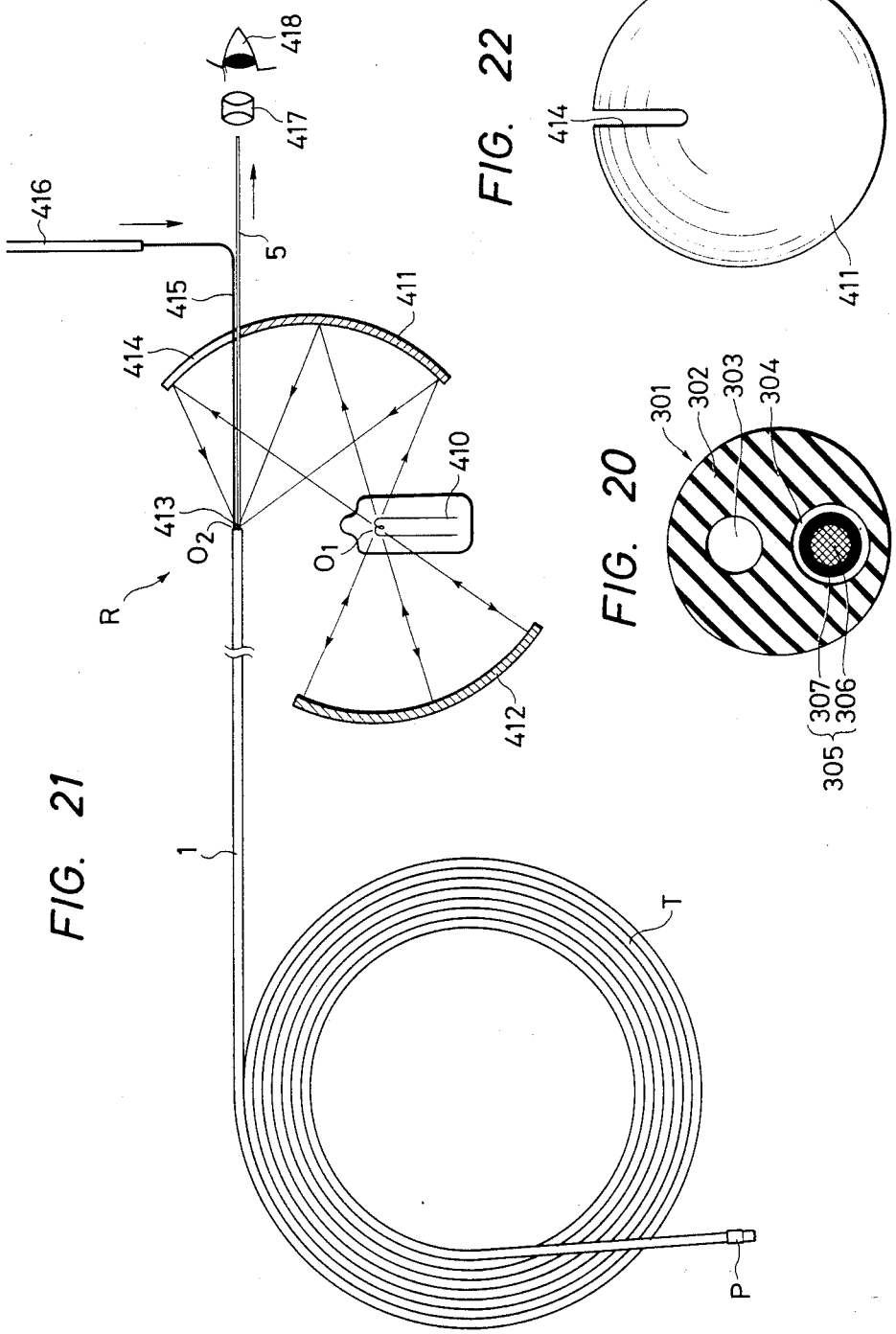

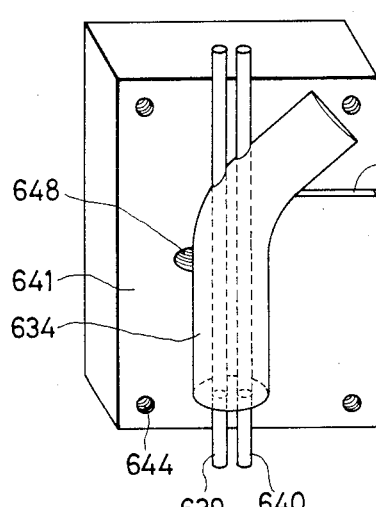
FIG. 28(a)
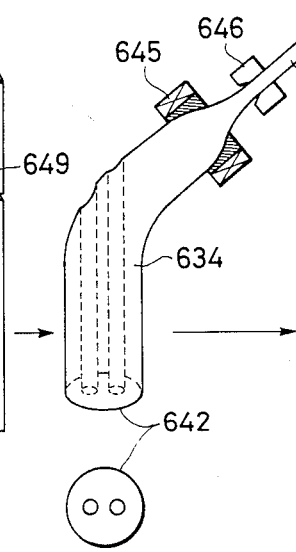
FIG. 28(b)
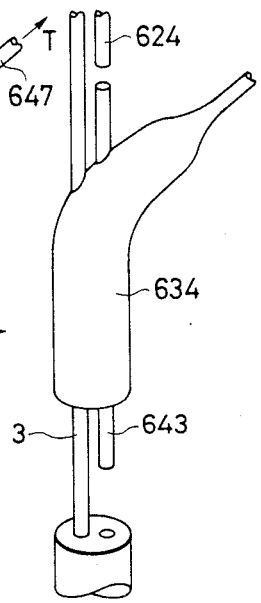
FIG. 28(c)
FIG. 29
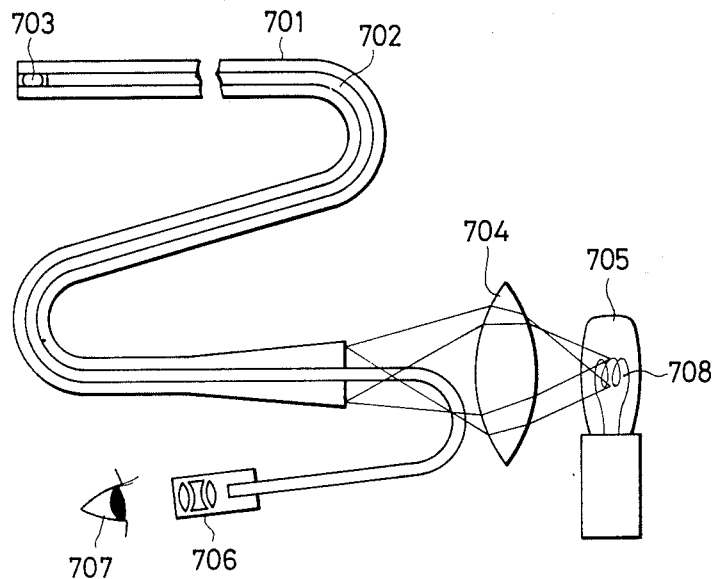

OPTICAL FIBER IMAGE SENSOR

This is a continuation of Ser. No. 836,217, filed on Feb. 28, 1986 abandoned which is a cntinuation of Ser. No. 519,333 filed on Aug. 1, 1983 abandoned.

BACKGROUND OF THE INVENTION

The present invention relates to an optical fiber sensor.

A catheter is a thin tubular surgical instrument which is inserted into a cavity of a living body to measure the attraction, absorption, and pressure of the liquid in the cavity.

Progressing a step further, an image catheter is an instrument which is used for observing the inside of the cavity, and which is constituted by an image fiber for transmitting an image, a fiber for transmitting illumination light and an outer cover.

FIG. 1 is a schematic diagram of the structure of one example of an image catheter.

The sensor optical fiber 1 is a thin flexible cable or tube to be inserted into the cavity of the body.

The sensor optical fiber 1 has, at its end, a branch mount 2 from which an image fiber 3, an illumination light transmitting optical fiber 4 and a saline solution tube 5 branch.

A direct viewing adaptor 6 is provided at the terminal of the image fiber 3 so that the observer can directly view the inside of the cavity.

A light source 7 is provided at the terminal of the illumination light transmitting optical fiber 4. The light from the light source 7 is transmitted through the light transmitting optical fiber in the sensor optical fiber 1 and projected onto the inside of the cavity to be observed.

A syringe 8 is attached to the terminal of the saline solution tube 5.

The forward end 9 of the sensor optical fiber 1 is inserted into a cavity in the body of a patient or the like. In this example, it is inserted into a blood vessel 10.

The blood vessel 10 is illuminated with light so that an image of the vessel is focused on the end surface of the image fiber 3 by a lens at the forward end 9. The image is transmitted as it is through the image fiber to the direct viewing adaptor 6 and enlarged thereat to be viewed by the observer.

When a blood vessel or the like is observed, the blood existing between the forward end of the catheter and the blood vessel wall becomes a bar to observation and therefore saline solution is injected by a syringe 8 so as to provide a flush of physiological saline solution 11 in the blood vessel 10 to thereby exclude blood therefrom.

FIG. 2 is a cross-section of the conventional sensor optical fiber for use for an image catheter.

The saline solution tube 5 and the image fiber 3 each have a circular cross-section of relatively large diameter and are separated from one another.

Numbers of thin illumination light transmitting optical fibers 4 are disposed in the space between the saline solution tube 5 and the image fiber 3.

The whole of the illumination light transmitting optical fibers 4, the image fiber 3 and the saline solution tube 5 is covered by an outer sheath 12.

In such an arrangement, however, the use efficiency of the available cross-sectional area for illumination light transmission relative to the entire outermost diameter is low, because the illumination light transmitting optical fiber has a circular cross-section. This is because space remains between the illumination light transmitting optical fiber, the saline solution tube, the image fiber, and the outer sheath.

To use the sensor fiber as an image catheter, there is a limitation in that the outer diameter should not exceed 2.3 mm, and this limitation has been a problem in providing an observing device of high efficiency.

In the case where such an image catheter is applied to a dental image fiber device, the configuration is as shown in FIG. 3.

The image fiber 3 and the illumination light transmitting optical fibers 4 are combined at the branch mount 2 and passed through a rigid pipe portion 13. The pipe portion 13 is inserted between a tooth 14 and a tooth-ridge 15 to observe the inside of the ridge 15. In some cases, a hole is bored in a tooth to observe the inside of the tooth.

FIG. 4 is an enlarged cross-section of the rigid tube portion 14

The image fiber 3 and the illumination light transmitting optical fibers 4 each having a circular cross-section are covered with a rigid outer sheath 12.

Since the image fiber 3 and light transmitting optical fibers 4 each having a circular cross-section are used, the volume efficiency is low.

Being inserted into a tooth or tooth-ridge, the rigid pipe portion must have a diameter nor larger than 0.7 mm. For this reason, there is a difficulty in providing the device and therefore this device has not yet been realized.

Endoscopy is widely used in industrial and medical fields. In an endoscope device, a light guide for guiding light and image fibers which are gathered into one flexible tube are generally used.

A light coupling system is required to guide light to the light guide from a light source. In the case where the diameter of the image fiber bundle including the light guide is required to be made especially thin, there are particular difficulties in the structure of the light coupling system.

In an endoscope, in many cases, it is required to apply illumination light to an object to be observed in order to obtain a clear picture image.

Conventionally, a method has been used in which illumination light is externally obtained or in which light from a light source is guided through a light guiding fiber bundle for transmitting illumination light.

In the latter case, the light guiding fiber bundle is provided separately from the image fiber so that it can be freely bent. Accordingly, the terminal of the light guide fiber bundle is directly connected to a light source independently of the image fiber.

FIG. 1A is a cross-section of an image receiving portion of an endoscope for explaining the conventional light coupling system.

An image fiber 42 and a light guiding fiber bundle 43 are separated from each other and are parallelly oriented in a flexible tube 44. An image receiving adaptor 41 is attached to a back end of the flexible tube 44. The light emitted from the back end of the image fiber 42 comes out of the image receiving adaptor 41 through an image receiving lens 45. This picture image is received by a TV camera so as to project the image on a monitor television display or, alternatively, is directly observed.

The light guiding fiber bundle 43 is coupled to a light source 46 through a light source communicating tube 47. There arises no difficulty in separating the image fiber from the light guide in the image receiving portion, because the light guiding fiber bundle is provided separately from the image fiber.

The endoscope is constituted by a forward end image pickup portion for receiving the image of an object, an intermediate long transmission portion and the back end image receiving portion. It is desirable to make the image pickup portion as thin as possible. An image pickup portion having a thin diameter is absolutely required in the case of an endoscope for medical use.

In an endoscope in which the image fiber and the light guiding fiber bundle are contained in the flexible tube in the separated state, the image pickup portion cannot be made sufficiently thin in diameter. The outermost diameter of the image pickup probe becomes 10 to 20 mm.

In many cases for industrial use, a fiber scope having such a thick diameter may be used. In the case for medical use, however, the conventional endoscope is limited to the observation of organs or viscera in which a device of this diameter can be inserted.

It is therefore desired to provide an endoscope having a thinner diameter. With an endoscope having a thinner diameter, the range of organs to be observed will be widened, contributing to an advance in medical treatment. It is not effective to only make thin the diameter of the image fiber. It is necessary to make the light guide for transmitting illumination light thin as well. If the cross-sectional area of the light guide is overly reduced, however, it will become difficult to transmit a sufficient amount of illumination light.

SUMMARY OF THE INVENTION

The present invention provides an optical fiber sensor including a first light transmission path and a second light transmission path, in which the first light transmission path defines therein a longitudinal space, and the second light transmission path extends within the space in the first light transmission path, whereby light transmission is possible both from one end of the first light transmission path to the other and from one end of said second light transmission path to the other.

The first light transmission path may include a transparent plastic tube for transmitting illumination light, and the second light transmission path may include a light receiving optical fiber which is inserted into or formed integrally with the illumination light transmitting transparent plastic tube.

BRIEF DESCRIPTION OF THE DRAWINGS

FIG. 7 is a cross-section of the dies, image fiber, light absorber and plastic for producing the sensor optical fiber, the cross-section of which is shown in FIG. 5, by extrusion molding;

FIG. 8 is a cross-section of the second die;

FIG. 9 is a perspective view showing an example of the branch portion of the sensor optical fiber, the cross-section of which is shown in FIG. 5;

FIG. 10 is a perspective view showing another branch portion;

FIG. 11 is a cross-section of the sensor optical fiber according to another embodiment of the present invention;

FIG. 12 is a cross-section of a dental sensor optical fiber to which the present invention has been applied;

FIG. 12A is a perspective view of the branch mount when the sensor optical fiber of the present invention is used.

FIG. 20 is a cross-section of a compound fiber in which a light guide and an image fiber are integrally formed.

FIG. 21 is a schematic diagram of the whole of the endoscope showing the light coupling system according to an embodiment of the present invention;

FIG. 22 is a front view of the first concave mirror;

FIG. 27 and FIGS. 28(a)–(c) describe a method used to produce a flexible light transmitting line; and FIG. 29 is a diagram illustrating another embodiment of the light transmitting fiber of the present invention.

DETAILED DESCRIPTION OF THE PREFERRED EMBODIMENTS

The invention will now be described with reference to the accompanying drawings.

Figure 5:
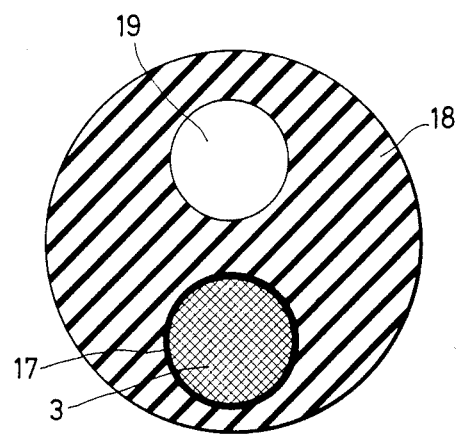
FIG. 5 is a cross-section of an improved sensor optical fiber.

In FIG. 5, the image fiber 3 is surrounded by a light absorbing layer 17 and the whole is covered by an illumination light transmitting transparent plastic body 18.

Illumination light transmitting optical fibers are not used. Instead, an integrated illumination light transmitting transparent plastic body 18 is used and a hole 19 for physiological saline solution is formed therein.

The outer diameter of the device has a limit of not larger than 2.3 mm.

The illumination light transmitting transparent plastic body 18, the image fiber 3, and the light absorbing layer 17 are integrally molded by an extrusion molding apparatus as shown in FIG. 7.

In FIG. 7, a sensor optical fiber is produced using first and second dies 21 and 22, respectively. The image fiber 3 is advanced through the first die 21. The light absorbing layer 17 is supplied into the first die 21, spreads to the periphery of the image fiber 3 and is extruded out of the first die 21, surrounding the image fiber 3.

The image fiber 3 covered by the light absorbing layer 17 is further passed through second die 22 and is extruded together with the illumination light transmitting transparent plastic body 18. The second die 22 is provided at its forward end with a hole-forming die portion 23 by which the physiological saline solution hole 19 is formed.

FIG. 8 is a cross-section of the forward end (bottom surface) of the second die.

In this manner, a sensor optical fiber having therein the image fiber 3 and the physiological saline solution hole 19 is produced by extrusion molding.

Thus, the branch portion must be different from that of the conventional device. FIG. 9 is a perspective view of an example of the branch portion.

At the portion following a position at which the branch is formed, the plastic parts other than the image fiber 3 are removed using undiluted sulfuric acid, with the image fiber 3 left as it is. A saline solution tube 24 is inserted into the physiological saline solution hole 19 and bonded thereat. The input of illumination light to the illumination light transmitting transparent plastic body 18 is performed in the following manner.

The light from a light source is guided by an illumination light transmitting auxiliary optical fiber 25 to a cross-section of branch 26. A polished mirror surface portion 27 is previously formed at a part of the branch cross-section 26 and the illumination light transmitting auxiliary optical fiber 25 is closely attached to the polished mirror surface portion 27 through matching oil.

FIG. 10 is a perspective view illustrating another branch portion. At the portion following the branch, the illumination light transmitting transparent plastic body 18 is cut open along its longitudinal direction to remove the image fiber 3. The saline solution conduit 24 is inserted into the physiological saline solution hole 19 and fixedly attached thereat. The cut open illumination light transmitting transparent plastic body 18 is heated and shaped to form a body of circular cross-section at the portion separated from the image fiber 3 and the saline solution tube 24.

In this manner, the coupling efficiency with the light source can be increased.

In the thus improved sensor optical fiber, the use efficiency of the available cross-sectional area for illumination light transmission relative to the entire outermost diameter is increased. This is because almost the entire portion other than the image fiber and the saline solution hole contributes to the transmission of illumination light.

Figure 6:
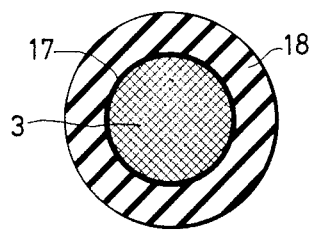
FIG. 6 is a cross-section showing an example of an improved dental image fiber.

When producing the dental sensor optical fiber, the device shown in cross-section in FIG. 6 is formed in a manner similar to that shown in FIG. 7. The image fiber 3 is provided at a central portion, the light absorbing layer 17 is provided to surround the image fiber, and the outer periphery thereof is covered with the illumination light transmitting transparent plastic body 18. The outer diameter is not larger than 0.7 mm.

Such a dental sensor optical fiber is integrally produced by using a die arrangement as shown in FIG. 7 by extrusion molding. In this case, however, no hole for the passage of saline solution is required.

FIG. 11 is a cross-section of a sensor optical fiber according to another embodiment of the present invention. The image fiber 3 is again covered with the light absorbing layer 17 in this embodiment.

To transmit illumination light, an illumination light transmitting transparent plastic tube 30 separately formed from the image fiber is used in place of the illumination light transmitting transparent plastic body integrally molded with the image fiber.

The illumination light transmitting transparent plastic tube 30 and the image fiber 3 are coaxially disposed with an annular hole 31 for physiological saline solution 31 formed therebetween.

The illumination light transmitting transparent plastic tube 30 and the image fiber 3 are produced separately from each other and the image fiber 3 is inserted into the illumination light transmitting transparent plastic tube 30 to constitute one sensor optical fiber.

The diameter of the hole is not larger than 2.3 mm.

The present embodiment may also be applied to the dental fiber. FIG. 12 is a cross-section of the dental optical fiber. There is no hole for saline solution. The image fiber 3 is covered by the light absorbing layer 17 and is then inserted into a hole formed in a illumination light transmitting transparent plastic tube. The outer diameter is not larger than 0.7 mm.

Although this example is similar to that shown in FIG. 6, the image fiber 3 and the transparent plastic tube 30 are not integrally molded but are produced separately from each other and thereafter insertion is performed to produce the sensor optical fiber.

As the image fiber 3, that is produced by the multiple method in which a plurality of optical fibers inserted in a silica tube are subjected to wire drawing, may be used.

The light absorbing layer 17 is applied to the outer periphery of the image fiber 3 in order to prevent noise light from entering A material such as silicone resin, into which carbon particles, having low transparency and a higher refractive index than silica (n=1.458) have been mixed, can be used.

The illumination light transmitting transparent plastic tube 30 is obtained by making a tube of a material having high transmittivity and a relatively high refractive index such as PMMA (polymethylmethacrylate), polystyrene, or polycarbonate. The refractive index is n=1.491.

Although it will do to use the transparent plastic tube 30 as it is, it is more preferable to provide a clad layer at the outer surface. If the outer surface of the transparent plastic tube 30 is coated with a clad layer of a plastic material having a slightly lower refractive index (about a 5% difference is sufficient) than the transparent plastic tube 30, factors such as scars and spots, which may lower the transmitting efficiency of the illumination light, can be eliminated. Further, if fluoro resin such as Teflon is applied as the outermost coating, not only can insertion be made smoothly, but protection from scars, spots or the like can be improved.

FIG. 12A is a perspective view showing an example of the structure of the branch mount 2 when the optical fiber sensor is used.

At the branch portion, the illumination light transmitting transparent plastic tube 30 is cut open and the image fiber 3 is removed from the tube 30.

A saline solution tube 32 is inserted into the illumination light transmitting transparent plastic tube 30 and adhered to the inner wall of the latter. A syringe is fixedly attached at the forward end of the saline solution tube 32.

The forward end of the image fiber 3 may connect to a direct viewing adaptor.

The portion following the cut open portion 31 of the illumination light transmitting transparent plastic tube 30 is shaped into a circular cross-section by heating or the like. Thus, the coupling efficiency with the light source can be increased.

With this embodiment, the efficiency of available cross-sectional area for illumination light transmission relative to the outermost diameter of the whole sensor optical fiber is high. Since a uniform transparent plastic tube is used instead of the conventional illumination light transmitting optical fibers having a circular cross-section, almost all of the portion other than the image fiber and the saline solution hole contribute to illumination light transmission. Further, the producibility is high and the cost of production is low. This is because the image fiber and tube are produced individually separately from each other, and thereafter the image fiber is inserted.

A thin image fiber system can be made according to this embodiment It has a small diameter along its entire length so that the branch and junction of the system can be conveniently provided A dental optical fiber sensor has been practically realized, because illumination light transmission is not performed by using a plurality of optical fibers.

The present invention can be applied to produce the following products:

(1) Image catheter (blood-vessel/heart endoscope); Catheter provided with hole for physiological saline solution.
(2) Endoscope for dental, ophthlmic, otorhinolaryngologic, and urinologic services.
(3) Sensor for measuring $SO_2$ and amount of heart pulsation. (In this case, an ordinary optical fiber is used instead of an image sensor).
(4) Spectroanalysis sensor for medical and industrial use. (In this case also, an optical fiber is used instead of an image sensor.)

A description will now be given respecting a fiber scope according to the invention, and particularly to the structure of a forward end portion of a fiber scope having a configuration such that an image fiber and an image pickup lens disposed at the forward end portion of the image scope are surrounded by a light guide.

Figure 13:
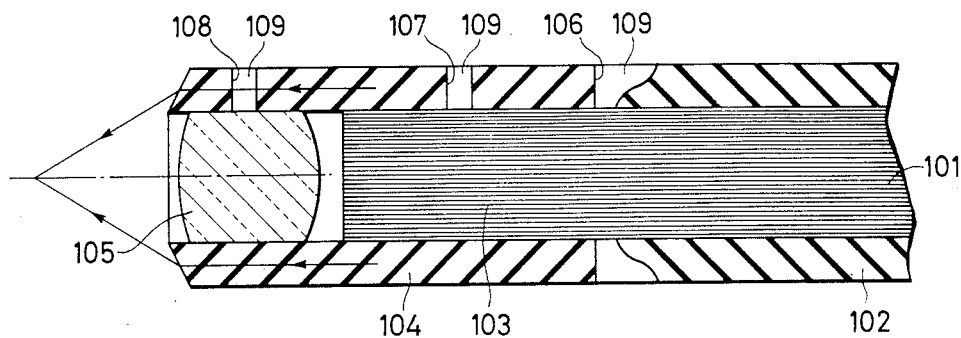
FIG. 13 is a cross-section, in the axial direction, of the forward end portion of an example of a fiber scope.

One fiber scope according o the invention is shown in FIG. 13, wherein a transparent plastic body 102 surrounding the outer periphery of an image fiber 101 and constituting a light guide is provided coaxially with the image fiber 101. However, the forward end portion of the image fiber 101 is not surrounded by the transparent plastic body 102 but surrounded by a transparent holder 104 which follows the transparent plastic body 102 to form the light guide. The transparent holder 104 is required to fix an image pickup lens 105 and the forward end of the image fiber 101 on the same axis with an accurate positional relationship so that the light passing through the image pickup lens 105 can carry the image of the object to the forward end surface of the image fiber 101. The image pickup lens 105 is inserted into the forward end portion of the transparent holder 104.

The space 106 between the forward end and the back end of the transparent plastic body 102 and the transparent holder 104, respectively, which constitute the light guide, is filled with a transparent resin adhesive 109. One or more through holes 107 and 108 are formed in the side wall of the transparent holder 104 such that the holes reach the forward end portion 103 of the image fiber and the image pickup lens 105. The transparent resin adhesive 109 is filled into these through holes 107 and 108 so as to adhesively fix the forward end portion 103 of the image fiber and the image pickup lens 105 to the transparent holder 104.

Figure 1:
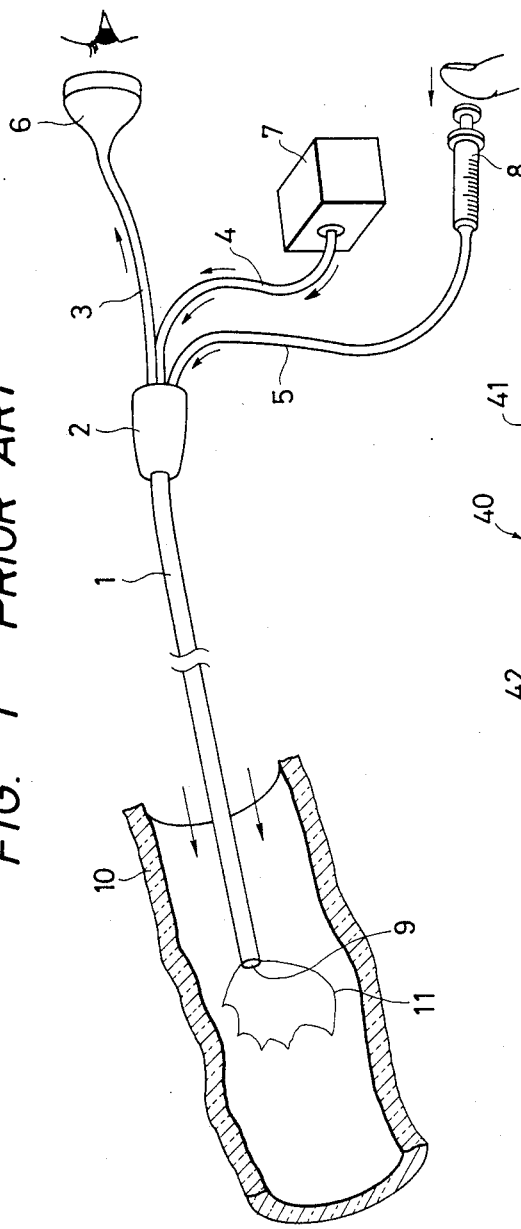
FIG. 1 is a schematic diagram illustrating an example of an image catheter.

Thus, illumination light transmitted from a light source as shown in FIG. 1 through the transparent plastic body 102 and the transparent holder 104 which constitute the light guide is radiated from the forward end surface of the transparent holder 104 onto an object. The light from the object is focused on the end surface of the image fiber 101 by the image pickup lens 105 and then transmitted through the image fiber 101 to a picture image observing portion as shown in FIG. 1 provided at the other end of the fiber scope.

The above-mentioned fiber scope, however, has a structure such that the light guide is axially separated into the transparent plastic body 102 and the transparent holder 104, which are bonded with an adhesive.

The fiber scope has limitations in strength and durability because of such structure at the forward end outer periphery, and because of the problem that the adhesive 109 has to satisfy the requirement of transparency since it constitutes a part of the light guide, sufficient adhesive strength cannot always be satisfied.

There is a further problem in that since the light transmitted through the light guide passes successively through the transparent plastic body 102, the transparent resin adherent 109 and the transparent holder 104, reflection is caused at the respective interfaces due to the difference of refractive indices of the materials, or different quality materials, to thereby increase the losses in light transmission in comparison with the case of transmission through one material only.

According to another embodiment, these shortcomings may be overcome.

Figure 14:
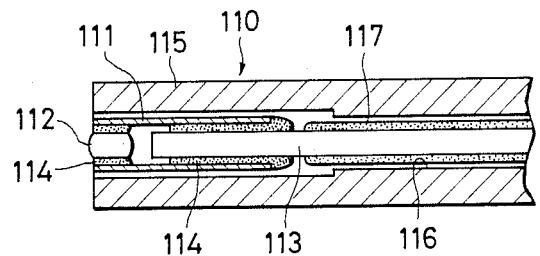
FIG. 14 is a cross-section, in the axial direction, of the forward end portion of the fiber scope according to the invention.

FIG. 14 is a cross-section, in the longitudinal direction of the forward end portion of another fiber scope 110 according to the present invention. A light guide 115 is formed into a cylindrical shape by extrusion molding or the like using a transparent resin such as PMMA (polymethylmethacrylate). A through hole 116 formed in the axial direction substantially at the central portion of its cross-section has an inner diameter which is large enough to be fit with an image fiber and has an enlarged inner diameter, at its forward end portion, which is large enough to fit on a cylindrical rigid sleeve (described later).

Figure 15:
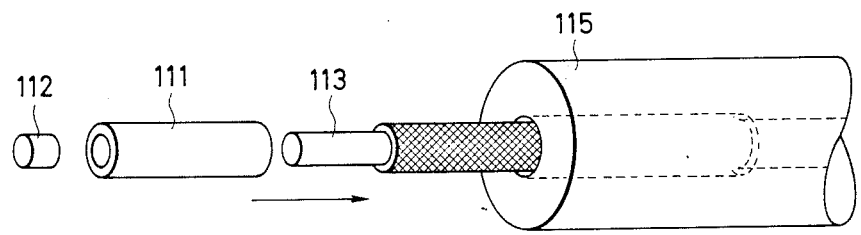
FIG. 15 is a perspective view illustrating the method of assembling the forward end portion of the fiber scope of FIG. 14.

As to the procedure of producing the fiber scope, and in particular, a sub-assembly as shown in FIG. 15, an image fiber 113 is passed through the through hole 116 of the light guide 115 and the end of the image fiber is made to slightly project out of the forward end of the light guide. The covering or protection layer 117 at the forward end portion of the image fiber 113 is removed. The forward end portion of the image fiber 113 from which the covering layer has been removed and an image pickup lens 112 are inserted into the cylindrical rigid sleeve 111 made of thin metal and are fixed with an adhesive 114, such as epoxy resin, applied to the periphery of the image pickup lens and the image fiber. At this time, the image pickup lens 112 is disposed at the forward end portion of the cylindrical rigid sleeve 111 and the image fiber is fixed while maintaining accurate positional relation with respect to the image pickup lens 112 such that the light passing through the image pickup lens 112 is focused on the forward end surface of the image fiber. The adhesive 114 is applied only to the outer periphery of the image pickup lens and image fiber, and therefore it is not necessary to select a transparent adhesive. This makes it possible to select the adhesive primarily on the basis of its adhesive strength.

The sub-assembly in which the image pickup lens 112, the image fiber 113 and the cylindrical rigid sleeve 111 are integrally fixed is drawn into the through hole of the light guide 115 and the end portion of the cylindrical rigid sleeve is caused to be made substantially flush with the forward end portion of the light guide. At this time, an adhesive is applied to the surface at and near the forward end of the through hole 116 of the light guide 115 so that the assembly composed of the image pickup lens 112, the image fiber 113 and the cylindrical rigid sleeve 111 is fixed to the light guide 115, thereby completing the forward end portion of the fiber scope 110. The thus produced fiber scope can be made to have a diameter of 0.6 to 6 mm at its forward end portion and can be widely suitably applied to various uses such as a fiber scope of the catheter type, a dental medical fiber scope, an industrial fiber scope, etc.

The fiber scope according to this embodiment of the invention has a structure such that an image pickup lens and the forward end of the image fiber are fixed in a cylindrical rigid sleeve so as to constitute an assembly and such that this assembly is inserted into and fixed in a light guide made of a single material and formed into an integral and substantially cylindrical shape. Accordingly, the light guide surrounding the outer periphery of the forward end portion of the fiber scope has a large strength and higher durability in comparison with the aforementioned structure in which a plurality of parts are bonded with a transparent adhesive, and, therefore, the fiber scope per se can be improved in strength and durability. Further, since a light guide made of one material and formed integrally is used, the loss in light transmission caused by light reflection at interfaces due to the plurality of parts constituting the light guide of the fiber scope and the transparent adhesive used in the same, can be eliminated, to thereby improve the efficiency of light transmission. A description will now be given with respect to the structure of a branch portion of a fiber scope, by way of example.

Referring back to FIG. 1, as described before, in order to obtain a field of view during observation in an opaque liquid such as blood, the forward end portion of an image pickup portion 9 is flushed with physiological saline solution so as to exclude blood in front of the forward end portion. In this case, as shown in FIG. 5, a flexible cable is used, in which the hole 19 for physiological saline solution is formed in the illumination light transmitting transparent plastic body 18 and an image fiber 3 is disposed in the illumination light transmitting transparent plastic body. At the branch portion, the illumination light transmitting transparent plastic body is cut open, as shown in FIG. 10, so that the above-described image fiber 3 and a saline solution tube 19 inserted into the physiological saline solution and coupled therewith, branch from the transparent plastic body.

In this case, there have been discovered problems as follows:

Because of a large cut-open portion of the illumination light transmitting transparent plastic body, the structure of transmission line deviates and the loss increases thereat; and The formation of the branch portion is difficult.

The present embodiment provides a novel branch portion in which the above-described defects are eliminated, as follows:

That is, the embodiment is characterized in that an illumination light transmitting transparent plastic body is formed with a hole bored from the outer periphery thereof, an image fiber is inserted thereinto, and a saline solution tube is coupled therewith, to thereby effectively suppress the light transmission loss.

Figure 16:
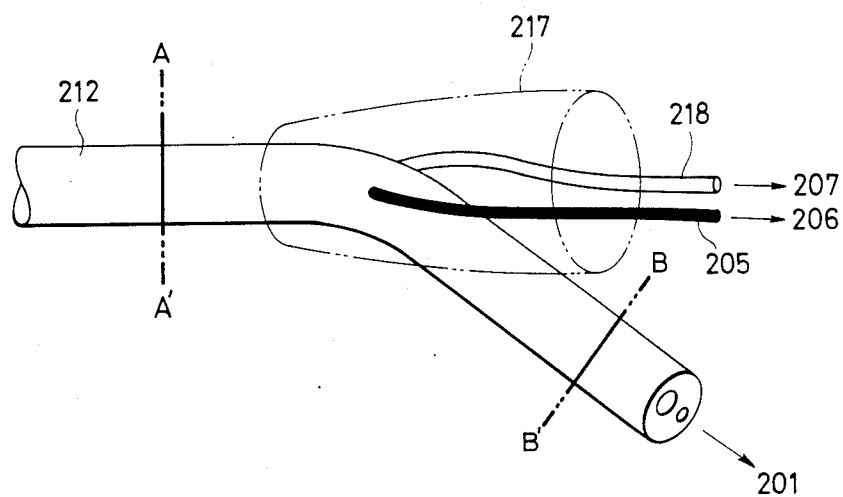
FIG. 16 is an illustration of a branch portion according to the invention.
Figure 17:
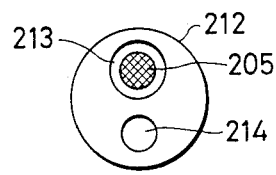
FIG. 17 is a cross-section taken along A—A' of FIG. 16.
Figure 18:
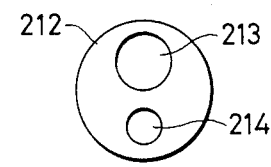
FIG. 18 is a cross-section taken along B—B' of FIG. 16.
Figure 19:
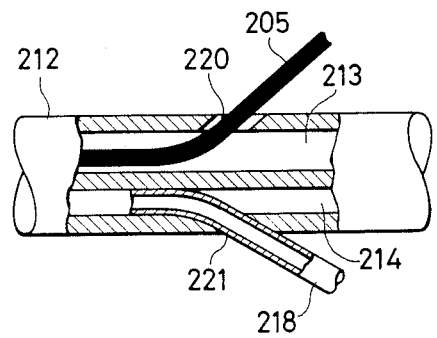
FIG. 19 is a longitudinal cross-section of the branch structure shown in FIG. 16.

As shown in FIG. 16, an image fiber 205 and a saline solution tube 218 are made to branch in a branch mount 217. FIG. 17 is a cross-section along the A—A' line of FIG. 16 and FIG. 18 is a cross-section along the B—B' line of the same. The illumination light transmitting transparent plastic body 212 used here is provided with not only a hole 214 for physiological saline solution but also with an image fiber inserting hole 213. The method is illustrated in FIG. 19. An image fiber inserting hole 220 and a saline solution tube inserting hole 221 are bored from the outer periphery of the illumination light transmitting transparent plastic body 212 corresponding to the image fiber inserting hole 213 and the physiological saline solution hole 214, respectively. The saline solution tube 218 is partially inserted into the physiological saline solution hole and bonded thereat.

This embodiment exhibits the following advantages:

The loss of illumination light at the branch portion from the illumination light transmitting transparent plastic body to the image fiber or the like is relatively small; and The formation of the branch portion is relatively easy.

Thus, the structure according to the present invention may be utilized as a branch portion of such devices as aforementioned.

FIG. 20 is a cross section of an optical fiber sensor similar to that shown in FIG. 5.

The compound fiber 30 has a one-piece fiber body. A transparent light guide 302 having a circular cross-section is the main part. The light guide 302 is made of a flexible transparent material such as PMMA (polymethylmethacrylate) resin.

The light guide 302 is produced by molding a plastic material extruded from a suitable die, and at this time a hole 303 for fluid and another hole 304 for passing an image fiber therethrough are simultaneously formed. The fluid passage 303 is for pouring/transmitting carbonic acid gas or physiological saline solution.

An image fiber 305 is made to pass through the hole 304. The image fiber 305 is composed of an image transmission portion 306 including a bundle of a plurality of glass and silica fibers and a light absorbing layer 307 covering the outer periphery of the portion 306.

As an example, the outer diameter of the compound fiber 301 is 3 mm, the diameter of the image fiber 305 is 0.6 mm, and the diameter of the image transmission portion for substantially transmitting picture images is 0.4 mm. The number of fiber strands (picture elements) of the image transmission portion is 3000.

Figure 1A:
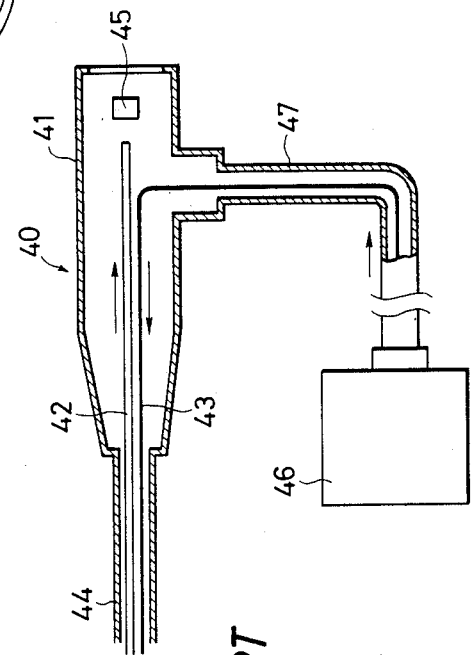
FIG. 1A is a diagram illustrating a portion of a conventional endoscope.
Figure 2:
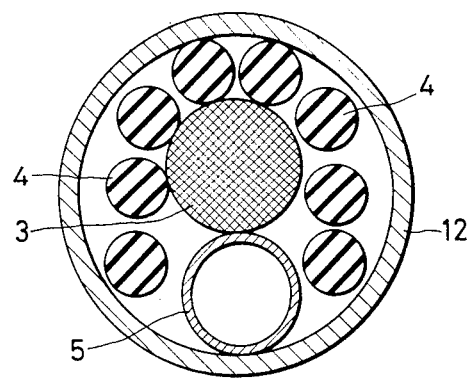
FIG. 2 is a cross-section of the conventional sensor fiber used as an image catheter.
Figure 3:
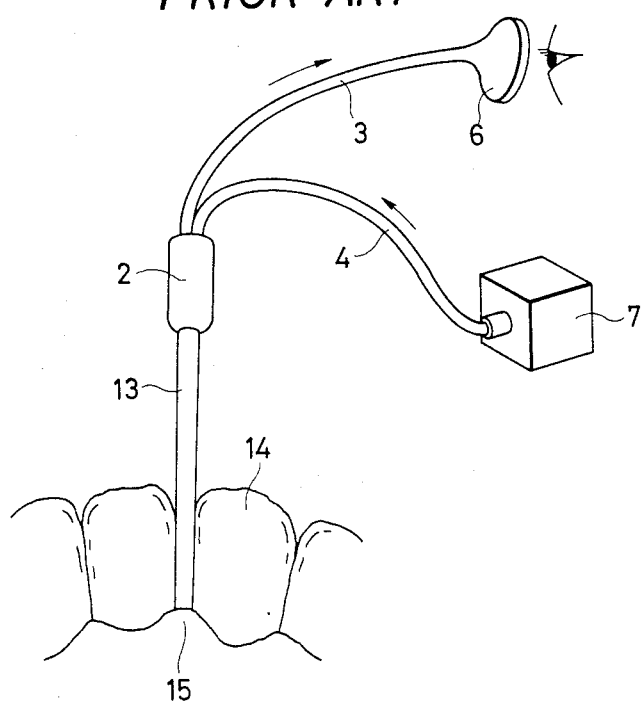
FIG. 3 is a diagram of a proposed configuration of an image catheter applied for dental use.
Figure 4:
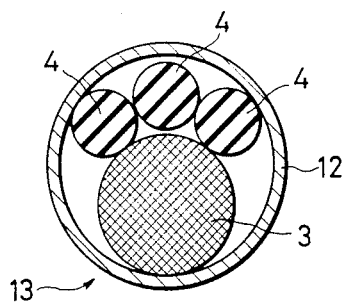
FIG. 4 is an enlarged cross-section of the rigid tube portion.

In such a compound fiber, the light guide and the image fiber are not separated from each other but are integrally formed. Accordingly, it is impossible to separately take out only the light guide fiber bundle so as to directly connect the same to a light source, as performed in the structure shown in FIG. 1A.

Further, it is difficult to lead light from a light source into the light guide because the light guide is very thin.

The compound fiber 301 may be called an image fiber with an outer peripheral light guide, since it has the light guide at the outer periphery thereof or may be called a light guiding ring-like path, since the light guide is disposed at a ring-like portion at the outer periphery in the cross-sectional view and the fluid passage 303 and the image fiber are disposed at or near the center. Accordingly, the term "light guiding ring-like path" means a light guide which is disposed at the outer periphery of the optical fiber device.

The following embodiment of the invention provides a light coupling system for leading illumination light into a thin light guiding ring-like path.

According to this embodiment, a concave mirror is used to lead light from a light source into an end surface of a light guiding ring-like path. The concave mirror is shaped and disposed so as to reflect light from the light source and focus the reflected light on the end surface of the light guiding ring-like path.

In order to increase the coupling efficiency, it is also effective to provide another concave mirror, separately from the above-mentioned concave mirror, for causing light emitted from the light source at the side opposite the fiber to return back to the light source.

The first concave mirror may be a spherical concave mirror, and, most preferably, it may be an elliptical concave surface mirror disposed such that that two focuses are made to agree with the light source and the end surface of the light guide ring-like path respectively.

A spherical concave mirror is suitably used as the second concave mirror

If it is necessary to pass the liquid pipe and the image fiber in a straight path, it is sufficient to provide a slot in the concave mirror to allow the pipe and image fiber to pass therethrough.

FIG. 21 is a schematic diagram illustrating the whole of an endoscope as an example of the light coupling system of this embodiment.

The endoscope is constituted of an image pickup portion P which approaches the object to be observed to receive the image therefrom, a long transmission portion T, and an image receiving portion R. The invention provides coupling between the light source and the light guide at the image receiving portion R. The structure of each of the image pickup portion P and the transmission portion T may be arbitrarily selected and may include apparatus according to other embodiments of the invention.

A light source such as a lamp 410 is placed in the vicinity of the image receiving portion R. The first and second concave mirrors 411 and 412 are placed behind and ahead of the light source 410, respectively.

The end surface 413 of the light guiding ring-like path (light guide 302), the light source 410 and the first concave mirror are disposed such that the light emitted from the light source is reflected by the first concave mirror and focused on the end surface 413 of the light guiding ring-like path.

The center of a filament of the light source 410 and the end surface of the light guiding ring-like path are selected as points $O_1$ and $O_2$, respectively.

It is sufficient to cause a real image of the light source to be produced on the end surface 413.

In this example, the filament and light guide were respectively 2 mm×3 mm in dimension and 3 mm in diameter. Since the light source is not a point source in the strict sense, a spherical concave mirror which may focus the image of $O_1$ onto $O_2$ may be used as the first concave mirror 411.

However, a spherical concave mirror has no capability of focusing light emitted from any one point onto another point. Having spherical aberration, the spherical concave mirror cannot strictly focus light from the light source onto the end surface 413 of the light guiding ring-like light path.

In the case where it is necessary to further increase the light coupling efficiency, one may use as the concave mirror an ellipsoid of revolution having focuses at the respective points $O_1$ and $O_2$. This is simply referred to hereinafter as an ellipsoidal concave mirror.

An ellipse has a characteristic such that a normal provided at any point on the ellipse always bisects the angle formed by the lines connecting the point and each of the two focuses. Accordingly, an ellipsoidal concave mirror can focus all the light emitted from one focus onto the other focus.

In the strict sense, it is thus preferable to use an ellipsoidal concave mirror having focuses at $O_1$ and $O_2$ as the first concave mirror 411.

The second concave mirror placed ahead the light source 410 reflects the light from the light source so as to cause it is to reflect back onto the first concave mirror. Since this light impinges onto the first concave mirror 411 in the same manner as that emitted from the focal point $O_1$, it is focused on the end surface $O_2$ of the light guiding ring-like light path.

The second concave mirror 412 can thus lead light oppositely emitted from the light source into the light guiding path to thereby increase the light coupling efficiency. Accordingly, a spherical concave mirror with the point $O_1$ as its center is the most suitable second concave mirror 412.

Figure 23:
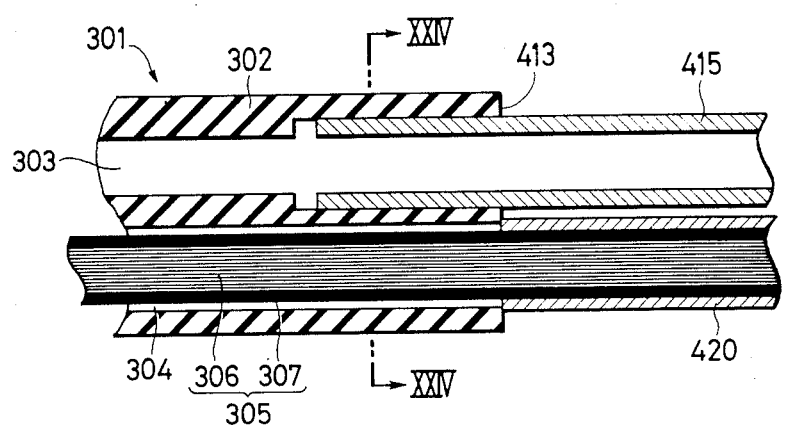
FIG. 23 is an enlarged longitudinal cross-section around the end surface of the light guiding ring-like path.
Figure 24:
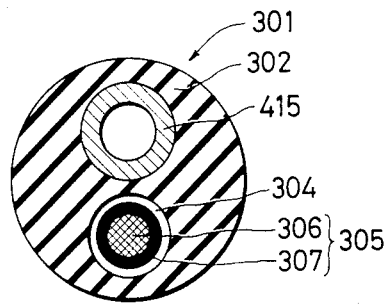
FIG. 24 is a cross-section taken along the XXIV—XXIV line in FIG. 23.

FIG. 23 is an enlarged cross-section around the end surface of the light guiding ring-like path. FIG. 24 is a cross-section along the XXIV—XXIV line in FIG. 23.

A metallic fluid pipe 415 extends from the end surface of the light guiding ring-like path 302 and is coupled to a flexible fluid delivery tube 416.

The image fiber 305 also extends from the end surface 413 of the light guiding ring-like path. The first concave mirror 411 is formed with a slot 414 so as to allow the image fiber 305 and the fluid pipe to pass therethrough. The image on the end surface of the image fiber 305 is observed by the eye 418 through a lens 417.

FIG. 22 is a front view of the first concave mirror 411. Since the slot 414 occupies only a small part of the reflecting surface of the mirror, the mirror function is not deteriorated. If the fluid pipe 415 and the image fiber 305 are sufficiently flexible to be bent, the slot 414 may be eliminated.

In FIG. 23, the metal fluid pipe 415 is inserted into the fluid passage 303 of the light guide 302 from the back end surface 413. The image fiber 305 is covered with an illumination light reflecting layer 420 on the outer surface of the light absorbing layer 307. This is for shielding the image fiber 305 from light from the strong light source. For example, a metal reflex film such as thin aluminum foil may be used.

According to the present embodiment, it is possible to cause the illumination light flux from the light source to efficiently impinge on the end surface of the light guide disposed at the outer periphery of the image fiber or the like. Even where the light guide has a thin diameter, the illumination flux can be throttled by a concave mirror and the light coupling efficiency is high.

When a slot 414 is formed in the first concave mirror, it is easy to replace the image fiber and/or the fluid pipe.

When the second concave mirror 412 is provided at the side opposite the first concave mirror 411 with respect to the light source, the light from the light source can be utilized more effectively.

Another embodiment of an improved branch structure according to the invention will now be described with reference to FIGS. 25 and 26.

There would be problems in cases where the branch portion arrangements shown in FIGS. 9, 10 and 12A are used, as follows:

In FIG. 9, it is difficult to mirror-surface polish even a portion of the cross-section of branch 26 under the condition that the image fiber extends therefrom. Also, the area of the cross-section of the auxiliary optical fiber 25 is small with respect to the area of the branch cross-section 26, so that the coupling efficiency with the light source is very low.

In FIGS. 10 and 12A, it is difficult to cut open the illumination light transmitting transparent body 18, because of the difficulty in separation from the fiber; and The light loss is large because the shape of the cross-section of the light guiding line changes extremely at the cut open portion.

Figure 25:
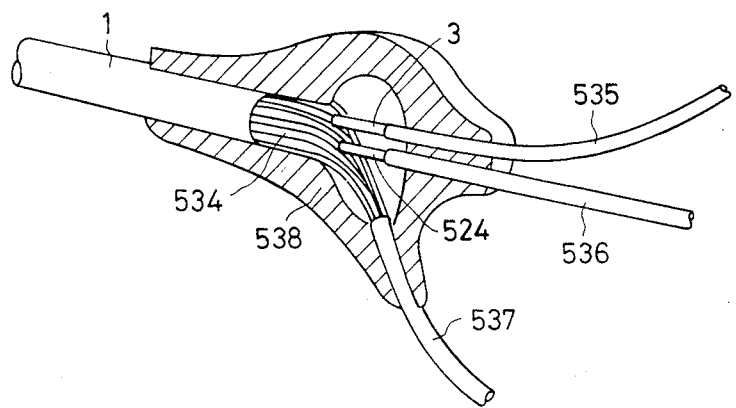
FIG. 25 is a diagram of a further embodiment of the present invention.

Referring to FIG. 25, a description will be given as to an improved branch structure. A transparent tube such as shown in FIG. 13 is used. In this case, assume that the transparent tube has such a shape as shown in FIG. 5, having two holes and having no image fiber 3. The end surface of this tube is polished to form a mirror surface thereat. An image fiber is inserted into one of the holes and a saline solution tube 524 is inserted into the other hole. An illumination light transmitting optical fiber bundle 534 is closely coupled to the light guide portion through matching oil or the like. The image fiber 3, the saline solution tube 524 and the illumination light transmitting optical fiber bundle 534 are provided with an image fiber cover 535, a tube cover 536 and a optical fiber bundle cover 537, respectively, and, then, fixed to a branch mount 538 (only one of the two halves is shown in the drawing).

Figures 26A, 26B, 26C:
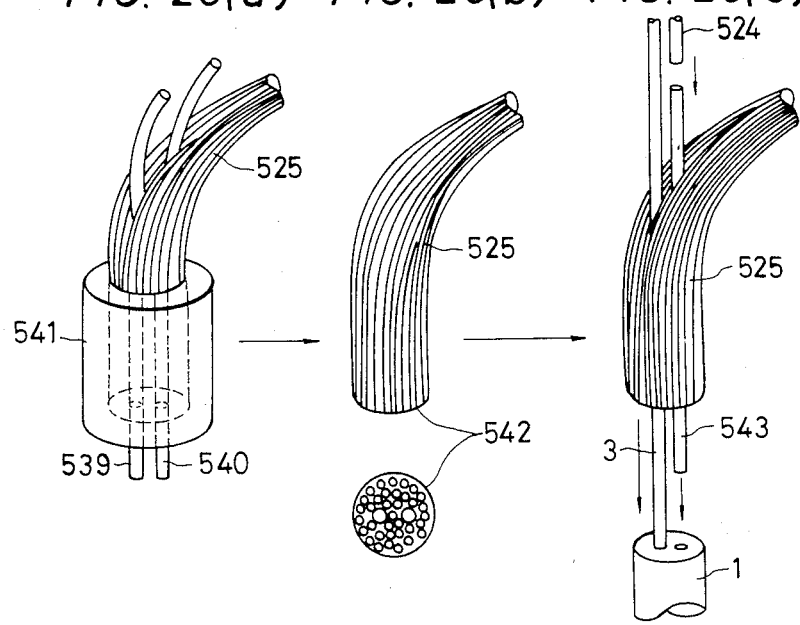
FIGS. 26(a)–26(c) is a diagram for explaining the method of producing an optical fiber of the present invention.

The method of producing the illumination light transmitting optical fiber bundle is the most important matter in providing the branch portion mentioned above. This will be described referring to FIGS. 26. In FIG. 26a, dummy tubes 539 and 540 made of Teflon ® or the like are inserted into a metal mold 541 to facilitate removal after processing. A plurality of optical fibers 525 are inserted in the space in the metal mold and an adhesive is poured thereto and hardened. Upon removal from the mold, the end surface 542 of the illumination light transmitting optical fiber bundle 525 is polished and the dummy tubes are pulled out, as shown in FIG. 26b. Next, in FIG. 26c, an image tube 3 is inserted into one of the holes and a connection pipe 543 (of stainless steel or the like) is inserted into the other hole. In this manner, the sensor optical fiber 1, the image fiber 3, the illumination light transmitting optical fiber bundle 525, and the physiological saline solution tube 524 can be coupled to each other. (For example, a good result was obtained with a bundle of about 15 optical fibers of 0.5 mm diameter coupled with a sensor optical fiber 1 of 2.3 mm diameter.

According to this embodiment, the following advantages can be obtained:

The efficiency of the coupling with the illumination light source is high; and

Production is relatively easy.

Figure 27:
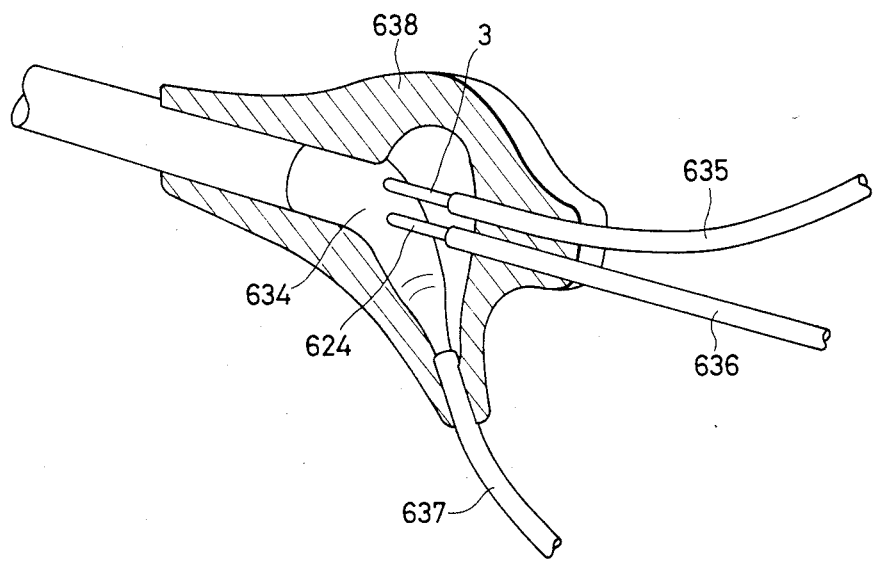

Another branching device is illustrated in FIGS. 27 and 28. The method of producing a molded illumination light transmitting line 634 is the most important matter in constructing the branch portion. This will be described by referring to FIGS. 27 and 28. In FIG. 28a, a metal mold 641 is mated with another mold member by engaging guide pins with guiding circular holes 644. Further, round rods 639 and 640 are inserted into the metal mold to form the two holes. Next, as shown in FIG. 28b, injection molding is performed by pouring a material (such as PMMA, polystyrene or polycarbonate) into the metal mold. Upon removal from the metal mold, the end surface 642 of the molded illumination light transmitting line 634 is polished, is passed through a ring heater 645 and then a die 646, and subjected to wire drawing by applying tension T, so as to produce a flexible light transmitting line 647.

Next, in FIG. 28c, an image tube 3 is inserted into one of the holes of the molded light transmitting line 634 and a connection pipe 643 (of stainless steel or the like) is inserted into the other hole. In this manner, the sensor optical fiber 1, the image fiber 3, the molded illumination light transmitting line 634, and the physiological saline solution tube 624 can be coupled to each other.

A description of another embodiment of a light transmission fiber according to the invention will now be described with reference to FIG. 29. This device is constituted such that an image fiber 762 is covered therearound by a plastic fiber 701 (made of, for example, PMMA (polymethylmetacrylate) mixed with a plasticizer) for the purpose of illumination as well as for the protection of the image fiber.

Only the incident end of the fiber, to which the light emitted from a light emission portion 708 of a light source 705 is applied via a coupling lens, is made thick in outer diameter so as to make it possible to effectively couple the light from the light source to the fiber 702. Further, the fiber is reduced at its emission end. The light passing through an image pickup lens 703 from an image to be observed is effectively transmitted by the optical fiber 702 so that an observation image can be viewed by the eye 707 through an eyepiece 706.

Since the light transmitting fiber according to this embodiment has an emitting end which is tapered to reduce its outer diameter with respect to that of the incident end, it is particularly effective where reduced diameter and high intensity illumination are required, as in a medical image fiber or the like, or in the case where reduced diameter and high energy transmission are required, as in a laser knife of the fiber type or the like.

What is claimed is:

1. A surgical device used in procedures in which said device is inserted into body tissue, said device comprising: a source of illumination light, a single first light transmission path and a second light transmission path, said first light transmission path defining therein a longitudinal space which completely surrounds the outer periphery of said second light transmission path, said second light transmission path extending in said space of said first light transmission path such that light transmission is possible both from one end of said first light transmission path to the other end thereof and from one end of said second light transmission path to the other and thereof; one end of both said first and second light transmission paths existing at a site under optical scrutiny; said first light transmission path including a transparent plastic tube for transmitting illumination light to said site to be illuminated, and said second light transmission path including a light receiving optical fiber inserted into said illumination light transmitting transparent plastic tube.

2. The device according to claim 1, wherein said light receiving optical fiber is an image fiber.

3. The device according to claim 2 wherein a light absorbing layer is applied to said image fiber.

4. The device according to claim 3, wherein a light absorbing layer is provided on an outer periphery of said image fiber.

5. The device according to claim 1, wherein said illumination light transmitting transparent plastic tube is made of material selected from the group consisting of polymethylmethacrylate, polycarbonate and polystyrene.

6. The device according to claim 1, wherein a fluid passageway is formed between said image fiber and said illumination light transmitting transparent plastic tube.

7. The device according to claim 1, wherein a transparent layer having a refractive index lower than that of said light transparent plastic tube is applied to the surface of said light transparent plastic tube.

8. The device according to claim 7, wherein a clad layer having a refractive index lower than that of said light transparent plastic tube is applied to the surface of said transparent layer.

9. The device according to claim 8, wherein said clad layer is made of fluororesin.

10. The device according to claim 1, wherein a clad layer is applied to the surface of said light transparent plastic tube.

11. The device according to claim 10, wherein said clad layer is made of fluororesin.

12. The device according to claim 1, wherein said second light transmission path includes an optical lens at its forward end for introducing light into said second light transmission path.

13. The device according to claim 12, further comprising a cylindrical sleeve, wherein said optical lens is inserted into and surrounded by said cylindrical sleeve, and said optical lens is coupled to said second light transmission path through said cylindrical sleeve to thereby form a sub-assembly, said sub-assembly being located at a forward end of said light transparent plastic tube.

14. The device according to claim 1, further including optical means for introducing light, emitted from a light source, into an end portion of said first light transmission path.

15. The device according to claim 14, said optical means including a concave mirror set at a predetermined angle.

16. The device according to claim 15, wherein said concave mirror has a radial slot.

17. The device according to claim 1, wherein said first path includes a light guide disposed at the periphery of a compound fiber defining a light guiding ring-like path, a light source provided in the vicinity of an end surface of said light guiding ring-like path, and a first concave mirror for reflecting light from said light source and for concentrating the reflected light onto said end surface of said light guiding ring-like path.

18. The device according to claim 17, in which a second concave mirror is provided at the side opposite said first concave mirror, for reflecting light from said light source back to said light source.

19. The device according to claim 17, in which an image fiber forms an inner portion of said compound fiber.

20. The device according to claim 17, in which a fluid passageway is continuously provided within said light guiding ring-like path.

21. The optical fiber sensor according to claim 17, in which said first concave mirror includes, as its reflection surface, an ellipsoidal- surface of revolution with a center of said light source and a center of said end surface of said light guiding ring-like path as its focuses.

22. The device according to claim 1, further including a branch portion structure, said respective transmission lines branching out from said branch portion, at which branch portion an end surface of said illumination light transmission line closely contacts a molded end surface of an optical fiber for leading illumination light from a light source.

23. The device according to claim 22, wherein a transparent body of plastics including PMMA, polystyrene, polycarbonate, is employed as said illumination light transmission line.

24. The device according to claim 22, wherein an image fiber is employed as said information line.

25. The device according to claim 1, said second path comprising an image fiber disposed within said single longitudinal space which totally encircles said image fiber and having a high transmission factor with respect to incident rays, said fiber sensor having an emitting and an incident end which are made thin and thick respectively.

26. The device according to claim 1, wherein said light receiving optical fiber is formed integrally with said illumination light transmitting transparent plastic tube.

27. The device according to claim 1, wherein a fluid passageway is formed axially of and within said first light transmission path.

28. The device according to claim 1, further including a branch portion wherein said first path is branched from said second path.

29. The device according to claim 28, including a light source guide input, said first path including a polished mirror surface for contacting said guide input.

30. A surgical device used in procedures in which said device is inserted into body tissue, said device comprising; a single first light transmission path and a second light transmission path, said first light transmission path defining therein a longitudinal space which completely surrounds the outer periphery of said second light transmission path, said second light transmission path extending in said space of said first light transmission path such that light transmission is possible both from one end of said first light transmission path to the other end thereof and from one end of said second light transmission path to the other end thereof; one end of both said first and second light transmission paths existing at a site under optical scrutiny; said second path including an image fiber, an image pickup lens being disposed o an axial line of said image fiber for focusing a picture image onto an end surface of said image fiber, and said first path including a light guide disposed substantially coaxially with said image fiber so as to surround said image fiber and said image pickup lens, said image pickup lens and the forward end portion of said image fiber being fixed in a cylindrical rigid sleeve so as to constitute a sub-assembly composed of said image pickup lens, said image fiber and said cylindrical rigid sleeve, and said light guide being made of a single material formed into an integral and substantially cylindrical shape such that said sub-assembly of said image pickup lens, said image fiber and said cylindrical rigid sleeve are inserted into and fixed in said light guide.

31. A surgical device used in procedures in which said device is inserted into body tissue, said device comprising; a single first light transmission path and a second light transmission path, said first light transmission path defining therein a longitudinal space which completely surrounds the outer periphery of said second light transmission path, said second light transmission path extending in said space of said first light transmission path such that light transmission is possible both from one end of said first light transmission path to the other end thereof and from one end of said second light transmission path to the other end thereof; one end of both said first and second light transmission paths existing at a site under optical scrutiny; wherein said second light transmission path branches from said first light transmission path through a hole formed therein passing through a side wall thereof to said longitudinal space.

32. The device according to claim 31, wherein an image fiber is employed as said second light transmission path.

33. The device according to claim 31, said first path including a longitudinal hole for guiding a fluid, and a hole passing through said first path from the outside to said longitudinal hole, a tube for supplying fluid being coupled to said longitudinal hole.

34. The device according to claim 31, wherein said hole formed in said first path is a bore, and said second path passes through said bore.

35. A surgical device used in procedures in which said device is inserted into body tissue, said device comprising; a source of illumination light, a single first light transmission path and a second light transmission path, said first light transmission path defining therein a longitudinal space which completely surrounds the outer periphery of said second light transmission path, said second light transmission path extending in said space of said first light transmission path such that light transmission is possible both from one end of said first light transmission path to the other end thereof and from one end of said second light transmission path to the other end thereof; one end of both said first and second light transmission paths existing at a site of an object under optical scrutiny; further including a branch portion structure, said first path comprising an illumination light transmission line for transmitting illumination light and said second path comprising an information transmission line for transmitting information light received from an object, said respective transmission lines branching out from said branch portion, at which branch portion an end surface of said illumination light transmission line closely contacts an end surface of an optical fiber bundle for leading illumination light from said source of illumination light.

36. The device according to claim 35, wherein a transparent body of plastics including PMMA, polystyrene, polycarbonate, is employed as said illumination light transmission line.

37. The device according to claim 35, wherein an image fiber is employed as said information line.

* * * * *